US009265282B2

(12) United States Patent
Miser et al.

(10) Patent No.: US 9,265,282 B2
(45) Date of Patent: Feb. 23, 2016

(54) SOLID ORAL SENSORIAL PRODUCTS INCLUDING STAIN INHIBITOR

(71) Applicant: Philip Morris USA Inc., Richmond, VA (US)

(72) Inventors: Donald E. Miser, Chesterfield, VA (US); William R. Sweeney, Richmond, VA (US); Qinglin Li, Richmond, VA (US); Jerome A. Merski, Midlothian, VA (US)

(73) Assignee: PHILIP MORRIS USA, INC., Richmond, VA (US)

( * ) Notice: Subject to any disclaimer, the term of this patent is extended or adjusted under 35 U.S.C. 154(b) by 84 days.

(21) Appl. No.: 14/033,112

(22) Filed: Sep. 20, 2013

(65) Prior Publication Data
US 2014/0093544 A1  Apr. 3, 2014

Related U.S. Application Data

(60) Continuation of application No. 13/591,031, filed on Aug. 21, 2012, now Pat. No. 8,568,801, which is a division of application No. 12/748,205, filed on Mar. 26, 2010, now Pat. No. 8,268,370.

(51) Int. Cl.
A24B 15/10 (2006.01)
A24B 15/18 (2006.01)
A23F 3/14 (2006.01)
A61K 47/02 (2006.01)
A23G 4/06 (2006.01)
A24B 13/00 (2006.01)
A24B 15/28 (2006.01)

(52) U.S. Cl.
CPC . *A24B 15/10* (2013.01); *A23F 3/14* (2013.01); *A23G 4/064* (2013.01); *A24B 13/00* (2013.01); *A24B 15/186* (2013.01); *A24B 15/287* (2013.01); *A61K 47/02* (2013.01); *A23V 2002/00* (2013.01)

(58) Field of Classification Search
USPC ........................... 424/751; 131/309, 352, 275
See application file for complete search history.

(56) References Cited

U.S. PATENT DOCUMENTS

| | | |
|---|---|---|
| 2,884,346 A | 4/1959 | Korth |
| 2,978,328 A | 4/1961 | Melzard et al. |
| 3,706,572 A | 12/1972 | Einstman et al. |
| 3,757,798 A | 9/1973 | Lambert |
| 3,927,683 A | 12/1975 | Wilson et al. |
| 4,289,147 A | 9/1981 | Wildman et al. |
| 4,347,859 A | 9/1982 | Bokelman et al. |
| 4,355,648 A | 10/1982 | Bokelman et al. |
| 5,311,886 A | 5/1994 | De Grandpre et al. |
| 5,598,868 A | 2/1997 | Jakob et al. |
| 5,601,097 A | 2/1997 | De Grandpre et al. |
| 5,773,062 A | 6/1998 | Cirigliano et al. |
| 5,895,680 A | 4/1999 | Cirigliano et al. |
| 6,298,859 B1 | 10/2001 | Kierulff et al. |
| 6,576,275 B1 | 6/2003 | Hoving et al. |
| 6,620,452 B1 | 9/2003 | Haddad et al. |
| 6,685,916 B1 | 2/2004 | Holme et al. |
| 6,786,220 B2 | 9/2004 | Bokelman et al. |
| 6,845,777 B2 | 1/2005 | Pera |
| 6,984,376 B2 | 1/2006 | Stephenson et al. |
| 7,445,769 B2 | 11/2008 | Holme et al. |
| 7,810,507 B2 | 10/2010 | Dube et al. |
| 7,861,728 B2 | 1/2011 | Holton, Jr. et al. |
| 8,268,370 B2 | 9/2012 | Miser et al. |
| 8,323,683 B2 | 12/2012 | Mody et al. |
| 8,336,557 B2 | 12/2012 | Kumar et al. |
| 8,469,036 B2 | 6/2013 | Williams et al. |
| 8,568,801 B2 | 10/2013 | Miser et al. |
| 2003/0056801 A1 | 3/2003 | Krauss et al. |
| 2003/0211184 A1 | 11/2003 | Hoving et al. |
| 2004/0136928 A1 | 7/2004 | Holme et al. |
| 2004/0224906 A1 | 11/2004 | Hoving et al. |
| 2005/0210615 A1 | 9/2005 | Shastry et al. |
| 2005/0244521 A1* | 11/2005 | Strickland et al. ............ 424/751 |
| 2006/0134020 A1 | 6/2006 | Robinson et al. |
| 2006/0191548 A1 | 8/2006 | Strickland et al. |
| 2007/0062549 A1 | 3/2007 | Holton, Jr. et al. |
| 2007/0186942 A1* | 8/2007 | Strickland et al. ............ 131/361 |
| 2007/0190157 A1 | 8/2007 | Sanghvi et al. |
| 2007/0298061 A1 | 12/2007 | Boghani et al. |
| 2008/0202536 A1 | 8/2008 | Torrence et al. |
| 2009/0208070 A1 | 11/2009 | Porsgaard et al. |
| 2009/0293889 A1* | 12/2009 | Kumar et al. ................. 131/275 |
| 2011/0083685 A1* | 4/2011 | Adams et al. ................. 131/310 |

(Continued)

FOREIGN PATENT DOCUMENTS

| | | |
|---|---|---|
| CN | 102274131 A | 12/2011 |
| DE | 4103209 C1 | 12/1992 |
| EP | 0483500 A1 | 5/1992 |

(Continued)

OTHER PUBLICATIONS

International Search Report mailed Aug. 4, 2011 for PCT/EP2011/001503.
International Preliminary Report on Patentability and Written Opinion mailed Oct. 11, 2012 for PCT/EP2011/001503.
Office Action (Notice of Ground for Rejection) issued on Mar. 11, 2015, by the Japanese Patent Office in Japanese Patent Application No. 2013-501675, and an English Translation of the Office Action. (9 pages).

Primary Examiner — Walter Webb
(74) Attorney, Agent, or Firm — Buchanan, Ingersoll & Rooney PC

(57) ABSTRACT

A solid oral sensorial product includes at least one botanical material and at least one phosphate containing stain inhibitor. The botanical material is selected from the group consisting of tobacco, tea, coffee, cocoa, and combinations thereof.

13 Claims, 5 Drawing Sheets

(56) References Cited

U.S. PATENT DOCUMENTS

2011/0083688 A1* 4/2011 Mishra et al. ............... 131/352
2011/0315154 A1* 12/2011 Mua et al. .................... 131/309

FOREIGN PATENT DOCUMENTS

| | | |
|---|---|---|
| EP | 2 540 172 A1 | 1/2013 |
| GB | 1180710 A | 2/1970 |
| GB | 1482060 A | 8/1977 |
| JP | 2010-508821 A | 3/2010 |
| JP | 2010-508822 A | 3/2010 |
| JP | 2010-534475 A | 11/2010 |
| JP | 2011-504733 A | 2/2011 |
| JP | 2013-507111 A | 3/2013 |
| WO | WO 99/40799 A1 | 8/1999 |
| WO | 2008-057963 A2 | 5/2008 |
| WO | 2008-057964 A2 | 5/2008 |
| WO | 2009-015142 A2 | 1/2009 |
| WO | 2011-042209 A1 | 4/2011 |
| WO | 2011-105418 A1 | 9/2011 |

* cited by examiner

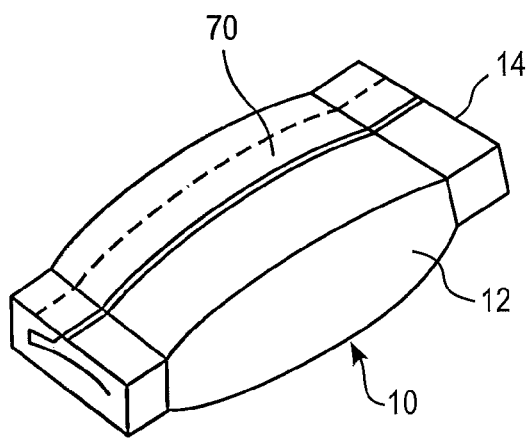
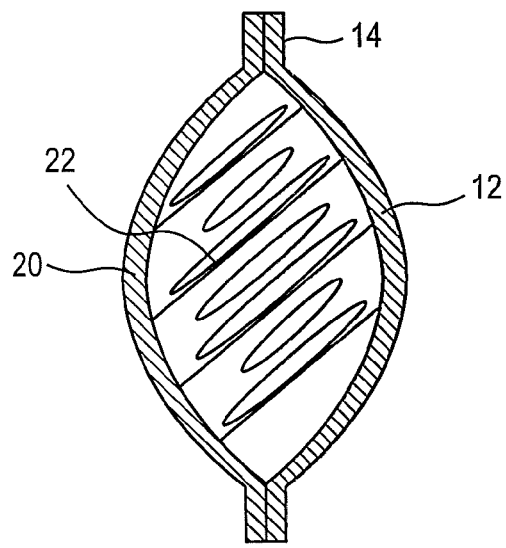
FIG. 1
FIG. 2
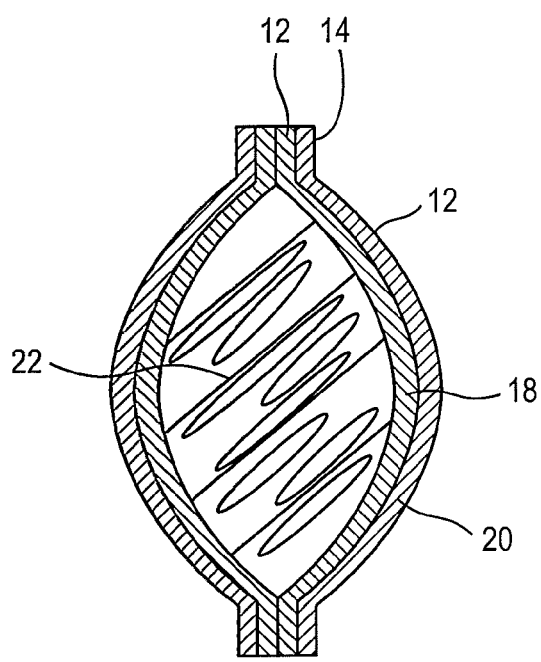
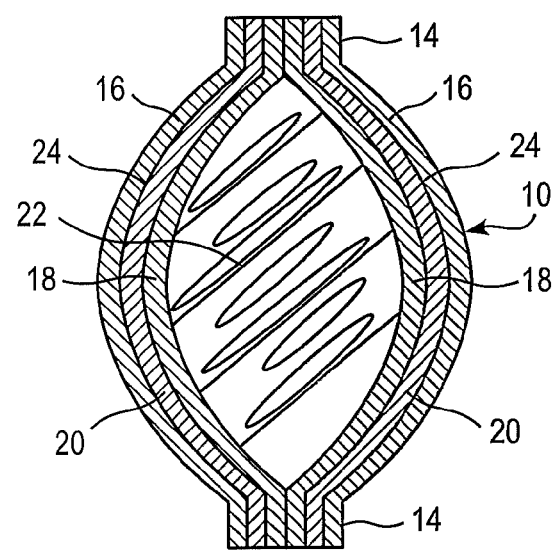
FIG. 3
FIG. 4

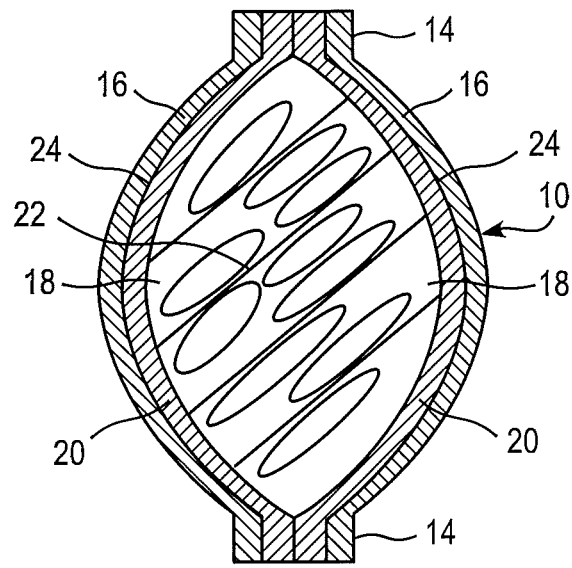
FIG. 5
FIG. 6
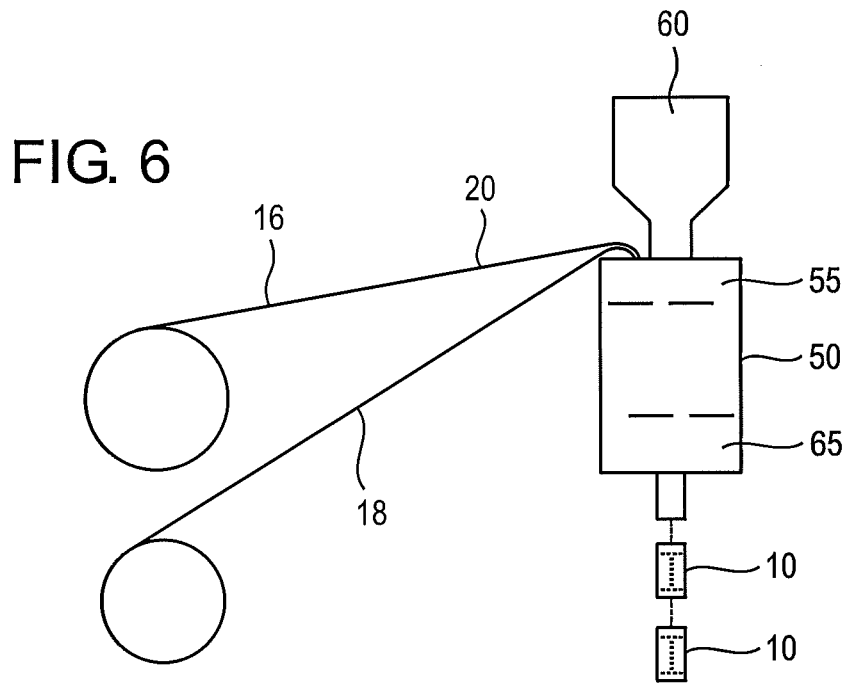
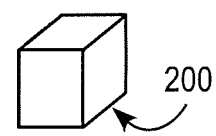
FIG. 7
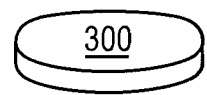
FIG. 8

100    110

Before Staining    SHMP & Snus    Snus
120    130    140

SOLID ORAL SENSORIAL PRODUCTS INCLUDING STAIN INHIBITOR

SUMMARY

Provided is a solid oral sensorial product comprising at least one phosphate containing stain inhibitor in an amount of about 0.001% to about 10.0% by weight based on the weight of the oral sensorial product; and at least one botanical material selected from the group consisting of tobacco, tea, coffee and combinations thereof. The phosphate containing stain inhibitor is selected from the group consisting of sodium hexametaphosphate, calcium hexametaphosphate, tripolyphosphate, and combinations thereof. The solid oral sensorial product contains about 25 mg to about 75 mg of the phosphate containing stain inhibitor, more preferably the oral sensorial product contains about 40 mg to about 60 mg of the phosphate containing stain inhibitor. The solid oral sensorial product weighs about 0.5 g to about 5.5 g. The solid oral sensorial product contains about 0.5 g to about 5.0 g of botanical material. Preferably, the phosphate containing stain inhibitor is sodium hexametaphosphate and the botanical material is tobacco.

The solid oral sensorial product is selected from the group consisting of oral pouch products, oral chews, tablets, moist smokeless tobacco, tobacco leaf products including loose leaf tobacco, plug tobacco, twist tobacco and tobacco bits, and combinations thereof. The oral pouch product comprises a filling material including the at least one phosphate containing stain inhibitor and the at least one botanical material; and a pouch wrapper for containing the filling material. The oral chew further comprises at least one polymer. The tablet comprises botanical powders.

Also provided is a method of making a solid oral sensorial product comprising: mixing at least one solid botanical material and at least one phosphate containing stain inhibitor to form a mixture; and forming a solid oral sensorial product from the mixture. The method also includes adding at least one additive to the mixture. The forming can comprise placing the mixture in a pouch wrapper to form an oral pouch product and molding the mixture to form a chew. Preferably, the phosphate containing stain inhibitor is added to the mixture in an amount of about 0.001% to about 10.0% by weight based on the weight of the oral sensorial product. Preferably, the phosphate containing stain inhibitor is added to the mixture as a powder. Alternatively, the phosphate containing stain inhibitor is added to the mixture as a solution. In an embodiment, the phosphate containing stain inhibitor can be added to the exterior of the product as a coating.

In an embodiment, the solid oral sensorial product can be a two-piece product including a first piece containing the phosphate containing stain inhibitor and a second piece containing the solid botanical material.

BRIEF DESCRIPTION OF THE DRAWINGS

FIG. 1 is a perspective view of an oral pouch product including at least one phosphate containing stain inhibitor.

FIG. 2 is a longitudinal cross-sectional view of a first embodiment of an oral pouch product including at least one phosphate containing stain inhibitor.

FIG. 3 is a longitudinal cross-sectional view of a second embodiment of an oral pouch product including at least one phosphate containing stain inhibitor.

FIG. 4 is a longitudinal cross-sectional view of a third embodiment of an oral pouch product including at least one phosphate containing stain inhibitor.

FIG. 5 is a longitudinal cross-sectional view of a fourth embodiment of an oral pouch product including at least one phosphate containing stain inhibitor.

FIG. 6 is a schematic illustration of a machine for forming the oral pouch product of FIG. 2.

FIG. 7 is an illustration of an oral chew including at least one phosphate containing stain inhibitor.

FIG. 8 is an illustration of an oral tablet including at least one phosphate containing stain inhibitor.

DETAILED DESCRIPTION

Figure 9:
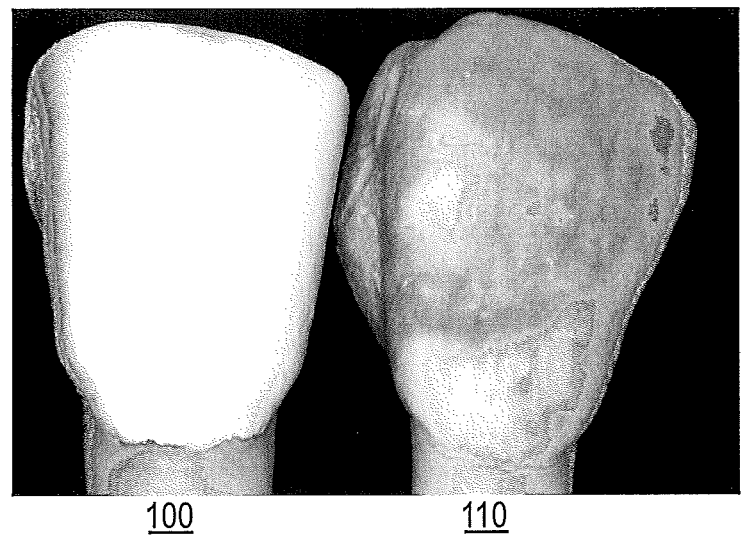
FIG. 9 is a photograph of a cow's tooth exposed to an oral pouch product including tea and at least one phosphate containing stain inhibitor and a cow's tooth exposed to an oral pouch product including tea and excluding a stain inhibitor.

Oral sensorial products can include tobacco, tea, coffee and the like, which can stain teeth. For example, tobacco contains polyphenols and metal ion complexes, which can discolor teeth. The oral sensorial products described herein include at least one phosphate containing stain inhibitor that provides phosphate that can bind polyphenols and metals to prevent staining of teeth and also chelate calcium so as to inhibit and/or reduce tooth staining during use of the oral sensorial product.

As used herein, the term "solid oral sensorial product" and "oral sensorial product" generally denotes solid oral products including smokeless tobacco, coffee, and/or tea, at least one phosphate containing stain inhibitor and optional additives, which can be placed in a user's mouth and enjoyed. The solid oral sensorial product may dissolve and/or disintegrate in the mouth. Alternatively, the solid oral sensorial product is removed from the mouth after use. The solid oral sensorial product can be a chew, a tablet, an oral pouch product, moist smokeless tobacco (MST), or the like, which can be placed in the mouth and enjoyed by a user.

As used herein, the term "oral pouch product" generally denotes a pouch product which fits in a user's mouth and delivers a desirable taste, aroma, chemesthetic effect or combination of two or more of these for enjoyment when placed in the oral cavity and contacted with the consumer's taste buds, olfactory receptors, or both, preferably via the consumer's saliva. The oral pouch product contains a filling material comprising tobacco, coffee and/or tea and at least one phosphate containing stain inhibitor contained in a pouch wrapper.

As used herein, the term "oral chew" generally denotes chewable oral products including at least one polymer and tobacco, tea and/or coffee. The oral chew can be chewed for a period of time ranging from 1 minute to 1 hour.

As used herein, the term "tablet" generally denotes oral products including botanical powder that is pressed to form a tablet, which can be placed in a user's mouth.

As used herein, the term "moist smokeless tobacco" (MST) generally denotes moist tobacco material that is placed between the cheek and gum so that juices from the tobacco material can be enjoyed by the user. The MST can be preportioned. Alternatively, a user can pinch off a portion and place in the mouth. Preferably, the MST is formed of shreds of moist tobacco material.

As used herein, the term "stain inhibitor" refers to substances capable of reducing the staining potential of tobacco and includes compounds that sequester, chelate or render staining compounds unsuitable for binding to teeth and/or blocks the active mineral sites of teeth to reduce the staining potential. Preferably, the stain inhibitors are phosphate containing stain inhibitors. Suitable stain inhibitors are selected from the group consisting of sodium hexametaphosphate, calcium hexametaphosphate, tripolyphosphate, and combinations thereof. In an embodiment, other phosphates, polyphosphates and/or phosphites can also be included in the oral sensorial product. In the preferred embodiment, the phosphate containing stain inhibitor is sodium hexametaphosphate.

As used herein, the term "nutraceuticals" refers to any ingredient in foods that has a beneficial effect on human health. Nutraceuticals include particular compounds and/or compositions isolated from natural food sources and genetically modified food sources.

A solid oral sensorial product including at least one phosphate containing stain inhibitor and methods of making the oral sensorial product are described herein. The solid oral sensorial product includes at least one botanical material selected from the group consisting of tobacco, tea, coffee and combinations thereof and at least one phosphate containing stain inhibitor. Optionally, the solid oral sensorial product can also include additives. Stain reduction of the solid oral sensorial product is accomplished by adding at least one phosphate containing stain inhibitor to the solid oral sensorial product in an amount sufficient to reduce and/or prevent staining of teeth as compared to solid oral sensorial products not including at least one phosphate containing stain inhibitor.

Botanical materials including tobacco, tea, and coffee include compounds that stain teeth. For example, tobacco includes staining compounds consisting of polyphenols that break down and form polyquinones having double conjugate bonds and other oxidized polyphenolics with double conjugate bonds which give tobacco its dark color, but also causes staining of teeth because the polyquinones and polyphenolics bond readily to tooth pellicle so as to immobilize the stain on the tooth surface and facilitate transport of metal ions, polyquinones and polyphenolics to the tooth crystal structure. In addition, tobacco includes metals, such as manganese and iron, which also act to stain teeth. In addition, since the mouth can contain too much calcium, softer irregular non-homogeneous calcium and/or glycoprotein structures which form in the pellicle can incorporate the staining material thus creating a brown calculus deposit on the tooth surface. The action of these and other staining compounds can be reduced by inclusion of at least one phosphate containing stain inhibitor in the solid oral sensorial product. Preferably, the stain inhibitor includes phosphates that can bond with polyquinones, chelate metals and thus prevent and/or reduce staining of teeth due to use of the solid oral sensorial products including tobacco, tea and/or coffee. The stain inhibitor works to inhibit staining by any fully senescent plant leaf material and/or extracts thereof, which contain metal ions including manganese and/or iron.

The amount of the stain inhibitor added to the solid oral sensorial product can vary depending on the stain inhibitor(s) chosen. In the preferred embodiment, the stain inhibitor is added to the solid oral sensorial product in an amount of about 25 mg to about 75 mg, more preferably about 40 mg to about 60 mg so that the stain inhibitor is included in the solid oral sensorial product in an amount of about 0.001% to about 10.0% by weight based on the weight of the solid oral sensorial product. The botanical material is included in the solid oral sensorial product in an amount of about 500 mg to about 5 g, more preferably about 1 g to about 3 g. For example, about 50 mg of stain inhibitor is effective for use in solid oral sensorial products including up to about 5 g of botanical material.

In a preferred embodiment, the stain inhibitor can be added to the solid oral sensorial product as a powder that is mixed with the botanical material. Alternatively, the stain inhibitor can be added an aqueous solution that is applied to the botanical material before and/or after forming the solid oral sensorial product. In an embodiment, the solution can be a non-aqueous solution.

Not wishing to be bound by theory, it is believed that the stain inhibitor acts in several ways to reduce and/or prevent staining of teeth by the tobacco, coffee and/or tea contained in the solid oral sensorial product. First, teeth are constantly changing either by dissolution of the enamel or by subsequent rebuilding of the enamel. Calcium and phosphate are key to the rebuilding of teeth. While the body provides calcium and phosphate, the stain inhibitor provides additional phosphate which can aid in the rebuilding of teeth. This can be useful, since saliva can be phosphate deficient. By rebuilding the teeth, fewer defects are available in the teeth where staining compounds can bind and/or discolor the teeth. Not wishing to be bound by theory, it is believed that the phosphate delivered by the solid oral sensorial product can help rebuild teeth during use of the solid oral sensorial product and also after use. Second, tobacco includes polyquinones having double conjugate bonds that darken the tobacco and stain teeth. The stain inhibitors described herein bond to the polyquinones and prevent them from binding to the teeth. Third, tobacco and other plant materials include metals, such as manganese and iron, which stain teeth. The stain inhibitors, such as sodium hexametaphosphate, chelate the manganese and iron to prevent staining by the metals.

In use, the stain inhibitor reduces and/or prevents discoloration of teeth, while maintaining the color of the tobacco, tea and/or coffee material used in the solid oral sensorial product. Thus, the color of the product is not changed by addition of the stain inhibitor to the product, which can be advantageous because some tobacco users rate the product based on the color of spit during use.

In the preferred embodiment, the at least one phosphate containing stain inhibitor is mixed with the botanical material, which is then used to form the solid oral sensorial product. Preferably, the stain inhibitor is mixed or incorporated with the botanical material to form a uniform mixture.

In a preferred embodiment, the botanical material is tobacco. Exemplary tobacco materials can be made of cut or ground tobacco and can include flavorants, additives and/or humectants. Examples of suitable types of tobacco materials that may be used include, but are not limited to, flue-cured tobacco, Burley tobacco, Maryland tobacco, nicotiana rustica, Oriental tobacco, rare tobacco, specialty tobacco, reconstituted tobacco, blends thereof and the like. In a preferred, embodiment, the tobacco material is pasteurized. In the alternative, the tobacco may be fermented. Preferably, the tobacco is fully browned tobacco such as barn cured Burley tobacco, Dark Air Cured or Fire Cured tobacco. Such fully browned tobacco has a high enzymatic production of polyquinones.

The tobacco material may be provided in any suitable form, including shreds and/or particles of tobacco lamina, processed tobacco materials, such as volume expanded or puffed tobacco, or ground tobacco, processed tobacco stems, such as cut-rolled or cut-puffed stems, reconstituted tobacco materials, tobacco beads, blends thereof, and the like. Genetically modified tobacco and other treated tobaccos may also be used. Also preferably, the tobacco material is smaller than about 20 mesh for ease of pouching.

In another embodiment, the botanical material is tea. Tea material can be provided in any suitable form, including, shreds and/or particles, processed teas, powders, extracts, combinations thereof and the like. The tea can be any type of tea including, without limitation, black tea, oolong tea, combinations thereof and the like.

In yet another embodiment, the botanical material is coffee. The coffee material can also be provided in any suitable form including whole bean, powders, extracts, and combinations thereof.

Optionally, the botanical material can include cocoa in the form of cocoa beans, cocoa powder, extracts and combinations thereof.

In a preferred embodiment, the botanical material can also include supplemental botanical material other than tobacco, tea and/or coffee. Suitable supplemental botanical materials include, without limitation, sugar beet fiber (Fibrex®), other vegetable fibers, herbs, spices, fruits and combinations thereof. Preferably, the supplemental botanical material is included in an amount of about 5% to about 45% by weight based on the weight of the botanical material. Even more preferably, the supplemental botanical material is included in an amount of about 10% to about 40% by weight based on the weight of the botanical material. These ranges for inclusion of the supplemental botanical material may be even further configured as follows: (a) about 20% to about 40% or (b) about 25% to about 35%.

In another embodiment, additives can also be added to the solid oral sensorial product. Suitable additives include, without limitation, humectants, flavorants, vitamins, minerals, nutraceuticals, energizing agents, soothing agents, sweeteners, coloring agents, amino acids, antioxidants, preservatives, acidity regulators and/or combinations thereof.

Humectants can also be added to the solid oral sensorial product to help maintain the moisture levels in the oral sensorial product. Preferably, the humectant, when included, is added to the botanical material. Examples of humectants that can be used include, without limitation, glycerol and propylene glycol. It is noted that the humectants can also be provided for a preservative effect, as the water activity of the solid oral sensorial product can be decreased with inclusion of a humectant, thus reducing opportunity for growth of micro-organisms. Additionally, humectants can be used to provide a higher moisture feel to a drier botanical component.

Suitable flavorants include any flavorants commonly used in foods, confections, smokeless tobacco products, tobacco articles, and/or other oral products. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as menthol, peppermint, spearmint, wintergreen, bourbon, scotch, whiskey, cognac, hydrangea, lavender, chocolate, licorice, citrus and fruit flavors, such as apple, peach, pear, cherry, plum, orange, lime, grape, and grapefruit, gamma octalactone, vanillin, ethyl vanillin, breath freshener flavors, butter, rum, coconut, almond, pecan, walnut, hazelnut, French vanilla, macadamia, sugar cane, maple, cassis, caramel, banana, malt, espresso, kahlua, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, peanut oil, lemon oil, ginger oil, balsamic vinegar, rice wine vinegar and red wine vinegar. Preferably, the flavorants are added to the solid oral sensorial product in an amount of about 0.1% to about 10% by weight based on the weight of the solid oral sensorial product. More preferably, the flavorants are added to the solid oral sensorial product in an amount of about 1% to about 5% by weight based on the weight of the solid oral sensorial product.

Preferably, the flavorants can be applied to the botanical material by spraying, coating, immersing, embossing, and/or dispersing the flavorants into or onto the botanical material. In an embodiment, the flavorants are added in the form of spray dried flavorants, essential oils, encapsulated flavorants, coacervated flavorants, colloidal encapsulated flavorants, suspensions, and/or solutions.

When the flavorants are encapsulated, the flavorants can also be provided by controlled release mechanisms such as pH change, heat activation, or mechanical activation through manipulating or sucking. In addition, flavorant capsules can have encapsulating coatings of various thicknesses so that the flavorants are released at varying rates to provide continuous or different flavor throughout use of the oral sensorial product.

In an embodiment, suitable sweeteners include, without limitation, monosaccharides, disaccharides, and polysaccharides, xylose, ribose, sucrose, maltose, mannitol, sorbitol, xylitol, fructose, glucose, mannose, sucralose, and combinations thereof. In an embodiment, the sweeteners can include non-carbohydrate sweeteners, such as aspartame, neotame, and saccharine. The amount of sweetener added to the oral sensorial product can vary based on the sweetener and/or combination of sweeteners used. For example, sucralose may be added to the oral sensorial product in an amount of about 0.1% to about 3% by weight based on the weight of the solid oral sensorial product. More preferably, sucralose may be added to the oral sensorial product in an amount of about 0.5% to about 1.5% by weight based on the weight of the solid oral sensorial product. Also for example, sugar can be added in an amount of about 5% to about 25% by weight based on the weight of the solid oral sensorial product. More preferably, sugar is added in an amount of about 10% to about 20% by weight based on the weight of the solid oral sensorial product.

Soothing agents can be included to provide a soothing sensation to the throat and oral cavity. Suitable soothing agents include, without limitation, chamomile, lavender, jasmine, and the like.

Suitable energizing ingredients include, without limitation, caffeine, taurine, and guarana.

Suitable vitamins include, without limitation, vitamin A (retinol), vitamin D (cholecalciferol), vitamin E group, vitamin K group (phylloquinones and menaquinones), thiamine (vitamin B1), riboflavin (vitamin B2), niacin, niacinamide, pyridoxine (vitamin B6 group), folic acid, choline, inositol, vitamin B12 (cobalamins), PABA (para-aminobezoic acid), biotin, vitamin C (ascorbic acid), and mixtures thereof. The amount of vitamins incorporated into a pouch product can be varied according to the type of vitamin and the intended user.

For example, the amount of vitamins may be formulated to include an amount less than or equal to the recommendations of the United States Department of Agriculture Recommended Daily Allowances.

Suitable nutraceuticals include, without limitation, various phytonutrients derived from natural plants and genetically engineered plants.

Suitable minerals include, without limitation, calcium, magnesium, phosphorus, iron, zinc, iodine, selenium, potassium, copper, manganese, molybdenum, chromium, and mixtures thereof. The amount of minerals incorporated into the pouch product can be varied according to the type of vitamin and the intended user. For example, the amount of minerals may be formulated to include an amount less than or equal to the recommendations of the United States Department of Agriculture Recommended Daily Allowances.

Suitable amino acids include, without limitation, the eight essential amino acids that cannot be biosynthetically produced in humans, including valine, leucine, isoleucine, lysine, threonine, tryptophan, methionine, and phenylalanine. Examples of suitable amino acids include the non-essential amino acids including alanine, arginine, asparagine, aspartic acid, cysteine, glutamic acid, glutamine, glycine, histidine, proline, serine, and tyrosine.

In another embodiment, the oral sensorial product can include various active agents having antioxidant properties that can delay the ageing process. For example, the active ingredients that can be extracted from *Ginkgo biloba* include flavonoid glycosides ("ginkgoflavonoids"), such as (iso) quercitin, kaempferol, kaempferol-3-rhamnosides, isorhamnetin, luteolin, luteolin glycosides, sitosterol glycosides, and hexacyclic terpene lactones, referred to as "ginkgolides" or "bilobalides." The active ingredients that can be extracted from *Camellia sinensis*, such as green tea, include various "tea tannins," such as epicatechol, epigallocatechol, epigallocatechol gallate, epigallocatechol gallate, theaflavin, theaflavin monogallate A or B, and theaflavin digallate. The active ingredients that can be extracted from *Vaccinium myrtillus*, such as blueberry, include at least 15 different anthocyanosides, such as delphinidin, anthocyanosides, myrtin, epimyrtin, phenolic acids, glycosides, quercitrin, isoquercitrin, and hyperoside. The active ingredients that can be extracted from *Vinis vitifera*, such as grapes, include polyphenols, catechols, quercitrins, and resveratrols. The active ingredients that can be extracted from *Olea europensis*, such as the leaves of olive trees, include oleuropein. Many active ingredients identified from these and other plant sources associated with the neutralization of free radicals and useful for delaying the ageing process are contemplated. The active ingredients of *Trifolium pratense*, such as purple clovers (i.e., common purple trefoils), include isoflavones or isoflavone glucosides, daidzein, genestein, formononentin, biochanin A, ononin, and sissostrin. The health-promoting properties of compounds derived from Panax, a genus that includes Ginseng, are well-established. These and other botanicals, botanical extracts, and bioactive compounds are contemplated.

Such botanical extracts can be prepared by various methods known in the art, including maceration, remaceration, digestion, agitation maceration, vortex extraction, ultrasonic extraction, countercurrent extraction, percolation, repercolation, evacoalation, diacolation, and solid/liquid extraction under continuous reflux. Other antioxidants known in the art are also contemplated.

Suitable preservatives for inclusion in the solid oral sensorial product include, without limitation, methyl paraben, propyl paraben, sodium propionate, potassium sorbate, sodium benzoate and the like.

Suitable acidity regulators for inclusion in the solid oral sensorial product include, without limitation, sodium carbonate, potassium carbonate, calcium carbonate and combinations thereof. Preferably, the acidity regulator is added in an amount sufficient to form an oral sensorial product having a pH ranging from about 6 to about 8.5. More preferably, the acidity regulator is added in an amount sufficient to form a solid oral sensorial product having a pH ranging from about 7 to about 8.

In a preferred embodiment, the solid oral sensorial product is sized and configured to fit comfortably in a user's mouth, preferably between the cheek and gum. A user can suck, chew, or otherwise orally manipulate the oral sensorial product to release the flavors contained therein.

Preferably, the solid oral sensorial product weighs about 0.1 g to about 5.5 g. These ranges for weight can be further restricted to (a) about 0.1 g to about 1.0 g, (b) about 1.0 g to about 2.0 g, (c) about 2.0 g to about 3.0 g, (d) about 3.0 g to about 4.0 g or (e) about 4.0 g to about 5.0 g. Also preferably, the oral sensorial product is about 0.25 inch to about 2.0 inches in width, about 0.25 inch to about 2.0 inches in length, and about 0.05 inch to about 2.0 inches thick. In an embodiment, the solid oral sensorial product is about 0.1 inch to about 2.0 inches in width, about 0.1 inch to about 2.0 inches in length and about 0.05 inch to about 1.0 inch thick.

The solid oral sensorial product may have a square, rectangular, quadrilateral, circular, moon, crescent, or oblong shape. The solid oral sensorial product can also be shaped like a half-moon or D-shape, or can take other shapes, including, without limitation oval, pouch-shape, rod-shape, cylindrical, tea leaf, tear drop, or hourglass shapes. In some embodiments, the shape can be similar to a ravioli or pillow shape. Other shapes may be utilized so long as the shapes fit comfortably and discreetly in a user's mouth.

Preferably, sharp corners are avoided as sharp corners may lead to oral discomfort. When the solid oral sensorial product is a pouch product, the web 12 (shown in FIG. 1) is sealed around one or more edges to contain the filling material 22 within the web 12.

The solid oral sensorial product can preferably deliver a plurality of flavorants to the user for a period of about 1 minute to about 3 hours. These ranges for flavor delivery can be further restricted to (a) about 5 minutes to about 75 minutes, (b) about 10 minutes to about 70 minutes, (c) about 15 minutes to about 65 minutes, (d) about 20 minutes to about 60 minutes, (e) about 25 minutes to about 55 minutes or (f) about 30 minutes to about 50 minutes. Preferably, the at least one hydrocolloid slows the release of tobacco flavors and juices from the oral sensorial product during use. Preferably, the solid oral sensorial product is discarded after a single use.

In an embodiment, the solid oral sensorial product is an oral pouch product including at least one phosphate containing stain inhibitor, at least one botanical material and a pouch wrapper. As described herein and illustrated in FIG. 1, an oral tobacco pouch product 10 comprises a pouch wrapper formed by a web 12 and a filling material 22 including the at least one phosphate containing stain inhibitor, the at least one botanical material and optional additives (shown in FIGS. 2 and 3) contained within the web 12. The oral tobacco pouch product 10 is designed to be placed in the mouth, preferably between the cheek and gum, for oral enjoyment.

As shown in FIGS. 1 and 2, the web 12 comprises an outer web 20 that is formed of a permeable or semi-permeable material, such that saliva can pass through the outer web 20 to the interior of the pouch product 10, and the flavors and juices from the filling material 22 contained within the interior of the pouch product 10 can be drawn out of the pouch and into the user's mouth.

In a preferred embodiment, outer web 20 comprises paper suitable for oral pouch products commonly referred to as "snus" or snuff. For example, the web can be formed of a cellulose fiber material, such as tea bag material or materials typically used to form snus pouches. Desirably, the outer web 20 of the porous pouch wrapper 12 is made from a material suitable for contact with food, such as materials used in packaging or handling foods. Preferred porous materials include, but are not limited to, films, gelatin, food casings, carrageenan, biopolymers, fabric (woven or non-woven), and/or paper such as filter paper, papers used to construct tea bags, coffee filters, and the like. Preferably, the material used to form the web 20 has a neutral or pleasant taste or aroma. Preferably, the material used to form the web 20 is selected to have desired properties of stain resistance, water permeability and/or porosity, and/or water insolubility.

Additionally, the materials used to form the outer web 20 can be provided with predetermined levels for basis weight and/or wet strength in order to reduce occurrence of breakage of the pouch wrapper 12 during manufacturing operations, storage and use. For example, an outer web 20 can be provided with a basis weight of about 5 to about 25 g/m$^2$, such as 5-10, 10-15, 15-20, or 20-25 grams/meters$^2$ (g/m$^2$) depending upon the final usage requirements, and/or a wet tensile cross-direction (CD) strength of about 15 to about 75 N/m, such as 15-30, 30-45, 45-60, or 60-75 Newtons/meter (N/m) depending upon the final usage requirements. One exemplary material is a tea bag material with a basis weight of about 16.5 g/m$^2$ with a wet tensile CD strength of 68 N/m.

It is also noted that the thickness of the outer web 20 can be varied to achieve desired levels of solubility through the pouch wrapper 12. For example, the paper can be about 0.1 mm to about 0.125 mm thick or about 0.07 mm to about 0.08 mm thick.

In a preferred embodiment, the web 12 maintains sufficient structural integrity during the time period that the web 12 is used so that the filling material 22 is retained therein. In an embodiment, flavorants may be added to the web 12 to deliver additional flavor to the user.

Preferably, as shown in FIGS. 2, 3 and 4, the filling material 22 comprises at least one botanical material selected from the group consisting of tobacco, tea, coffee and combinations thereof, at least one phosphate containing stain inhibitor and optional additives. Preferably, the filling material 22 has a moisture content of about 5% to about 50%. More preferably, the filling material 22 has a moisture content of about 12% to about 25%. Even more preferably, the filling material 22 has a moisture content of about 15% to about 20%.

For example, in one embodiment, the oral tobacco pouch product 10 can comprise a web containing about 5 g tobacco material, about 50 mg sodium hexametaphosphate, peppermint oil, and sugar beet fiber. In other embodiments, the oral tobacco pouch product 10 can comprise a web containing tobacco material, about 50 mg tripolyphosphate and peppermint oil.

As shown in FIG. 1, in one embodiment, the oral tobacco pouch product 10 comprises a longitudinal seam 70. The longitudinal seam 70 can comprise overlapping sections of the outer web 20. Preferably, the oral tobacco pouch product 10 also includes at least one transverse seam 14. The transverse seams 14 can be formed such that the inner surface of the outer web 20 of the pouch wrapper 12 another section of the inner surface of the outer web 20 to form the transverse seam 14 (shown in FIG. 2).

As shown in FIG. 3, the web 12 may comprise an inner web 18 and an outer web 20. In the preferred embodiment, the inner web 18 can be made of the same materials as the outer web 20. In other embodiments, the inner web 18 can be made of a different material than the outer web 20. In another preferred embodiment, the inner web 18 reduces the tendency of the filling material 22 to discolor (stain) the outer web 20. The inner web 18 reduces staining of the outer web 20 by reducing the opportunity for moisture from the filling material 22 or its additives to reach the outer web 20 prior to use. The inner web 18 also allows the moisture content and other constituents of the filling material 22 to be maintained in its original (fresh) condition until use.

With reference to FIG. 4, the web 12 may comprise an outer web 20, an inner web 18, and a coating 16 applied to an outer surface 24 of the outer web 20 to form a coated web. Preferably, the coating 16 also includes at least one phosphate containing stain inhibitor so as to provide phosphates to the user's mouth upon placement of the oral product therein. In a further embodiment, the coating can release flavorants or other ingredients to the user's mouth when in contact with saliva.

With reference to FIG. 5, the web 12 may comprise an outer web 20 and a coating 16 applied to an outer surface 24 of the outer web 20. A filling material 22 is contained within the outer web 20.

Preferably, the coating 16 includes at least one flavorant and/or other additives, such that the coating 16 rapidly releases at least one flavorant and/or other additives, such as sweeteners, when inserted into an oral cavity. In the preferred embodiment, the coating 16 also includes at least one phosphate containing stain inhibitor. Additionally, the coating 16, the outer web 20 and/or the inner web 18 can include humectants that soften the web 12 during use, such that the web 12 is comfortable in the mouth of a user.

In one embodiment, the coating 16 comprises at least one polymer, a negligible amount of water and at least one flavorant. In another embodiments, the coating 16 comprises at least one flavorant, at least one phosphate containing stain inhibitor and at least one sweetener. In an embodiment, the coating 16 can also include additives, such as sweeteners and/or humectants. In other embodiments, the additives described below can also be included in the coating 16.

In one embodiment, the coating 16 is water-soluble, such that the coating 16 rapidly dissolves and releases one or more flavors and/or the at least one phosphate containing stain inhibitor when placed in a user's mouth. In another embodiment, the coating 16 is water insoluble. In an embodiment, the coating 16 may include a cross-linked polymer. The amount of cross-linking can be varied to alter the rate of dissolution of the coating 16. Preferably, the viscosity of the coating 16 prior to application is about 600 cps to about 6,000 cps, but may be higher of lower depending on the coating formulation and/or method of application to the inner paper layer.

The coating 16 can include synthetic and/or natural polymers. Exemplary polymers include, without limitation, hydrocolloids, polysaccharides, food proteins, and the like. The polymers can be cross-linkable or non-cross-linkable or combinations thereof.

Suitable non-chemically-cross-linkable polymers include, without limitation, starch and starch derivatives, such as modified starch, dextrin, gums, such as gum arabic, guar gum, xanthan gum, locust bean gum, curdlan gum, gellan gum, fenugreek derivative gums, pullulan, chitosan, chitin, cellulose and cellulose derivatives, synthetic polymers, such as polyvinyl alcohol, polylactide, polyethylene glycol, polyvinylpyrrolidone, or polyvinylacetate, proteins, such as gelatin, zein, soy protein, rice protein, and whey protein, and soluble or insoluble vegetable fiber.

Suitable chemically cross-linkable polymers include, without limitation, alginate, pectin, carrageenan, and modified polysaccharides with cross-linkable functional groups.

When a cross-linking agent is used, the cross-linking agent is a polyvalent metal salt, more particularly, a monovalent metal ion salt or bivalent metal ion salt. While, both monovalent and bivalent metal ion salts may be used, a bivalent metal ion salt is particularly suitable for crosslinking certain polysaccharides, such as pectins. Suitable cross-linking agents include, without limitation, calcium lactate, calcium chloride, calcium lactobionate, tricalcium phosphate, calcium glycerophosphate, calcium hexametaphosphate, calcium acetate, calcium carbonate, calcium bicarbonate, calcium citrate, calcium gluconate, sodium chloride, sodium lactate, sodium acetate, sodium carbonate, sodium bicarbonate, sodium citrate, sodium gluconate, potassium chloride, potassium lactate, potassium acetate, potassium carbonate, potassium bicarbonate, potassium citrate, potassium gluconate and combinations of these.

The coating 16 can include encapsulated flavorants in the form of beads and/or microcapsules embedded therein. The beads and/or microcapsules can contain controlled release flavorants and/or other additives, such as sweeteners, humectants and the like.

The coating 16 preferably dissolves in about 0.1 second to about 30 seconds. These ranges for coating dissolution may be even further restricted to (a) about 1 second to about 25 seconds, (b) about 2 seconds to about 20 seconds, (c) about 3 seconds to about 15 seconds or (d) about 4 seconds to about 10 seconds after introduction into the oral cavity.

Preferably, the coating 16 is applied to a first side 24 of the outer web 20 as a solution, suspension and/or emulsion. For example, the desired ingredients of the coating 16 can be mixed to form a solution, which is then transferred to the first side 24 of the outer web 20 which preferably has a heat sealable adhesive layer on the opposite side. In an embodiment, the outer web 20 includes an adhesive layer on a surface facing the inner web 18. Suitable methods for applying the coating 16 to the first side 24 of the outer web 20 include spray, slot die and/or gravure application methods.

In a preferred embodiment, the coating 16 is added in an amount of about 1 g/m$^2$ to about 50 g/m$^2$ on a dry weight basis to the inner web and the coating, when dried, can have a moisture content of about 5% to about 8%.

To form the filling material, the tobacco material, at least one phosphate containing stain inhibitor, optional additives and optional supplemental botanical material are mixed to form a substantially uniform filling material.

Oral tobacco pouch products 10 are continuously formed by introduction of predetermined amounts of the filling material 22 into the tubular form above a transverse seam, formation of an upper transverse seam above the filling and cutting the tubular formation at locations along the length of the tubular formation to form individual pouches.

Sealing may be accomplished by any suitable sealing method, such as, for example, adhesive or by mutual sealing. Mutual sealing may be thermal or sonic. Preferably, sealing is accomplished by thermal sealing. Preferably, the inner web is paper with a flavor coating on one side and is sized to avoid becoming part of the longitudinal seam.

As shown in FIG. 7, the solid oral sensorial product can be a chew 200 including at least one botanical material, at least one phosphate containing stain inhibitor and optional additives. The chew can also include optional polymers.

As shown in FIG. 8, the solid oral sensorial product can be a tablet 300 including botanical powder and at least one phosphate containing stain inhibitor. The tablet can be formed by compressing the mixture of botanical powder and stain inhibitor. Preferably, the tablet has a diameter of about 0.5 cm to about 2.0 cm, and can be placed in a user's mouth.

The solid oral sensorial products described herein provide reduced staining of teeth as compared to solid oral sensorial products not including the phosphate containing stain inhibitors as described herein.

To determine the effectiveness of the phosphate containing stain inhibitor on oral sensorial products including tea, a test was performed to simulate 6 months of use of the oral sensorial products. About 187.5 mL artificial saliva and 75 pouches containing 5.0 g tea were placed in a bag in a water bath at 100° F. for 3 minutes. The artificial saliva was formed as part of a 1000 mL batch including 4.20 g sodium bicarbonate, 0.50 g sodium chloride and 0.20 g potassium carbonate. The bag was removed and rolled for about 2 minutes and then returned to the water bath for 10 minutes. This process was repeated four more times (five total). The pouches were then removed from the bag and 50 mL of the extract was placed in a 250 mL crystallization beaker. Cow's teeth were then immersed in the 50 mL of extract, the beaker was covered with polypropylene wrap, and the teeth were soaked for 7 minutes at about 100° F. The teeth were removed from the beaker and rinsed with reverse osmosis water for about 5 seconds. The front enamel of each tooth was brushed with 1 g of Crest® Cavity Protection toothpaste for 30 seconds, rinsed with reverse osmosis water and covered to prevent exposure to light. This regime was repeated 4 additional times (5 total). A second extract was made using pouches including 5.0 g tea and 50 mg sodium hexametaphosphate. A second set of cow's teeth were soaked in the extract 5 times as described above. The Cow's teeth exposed to sodium hexametaphosphate and tea 100, as shown in FIG. 9, are noticeably lighter in color when compared to cow's teeth exposed to oral pouch products including tea alone 110.

Figure 10:
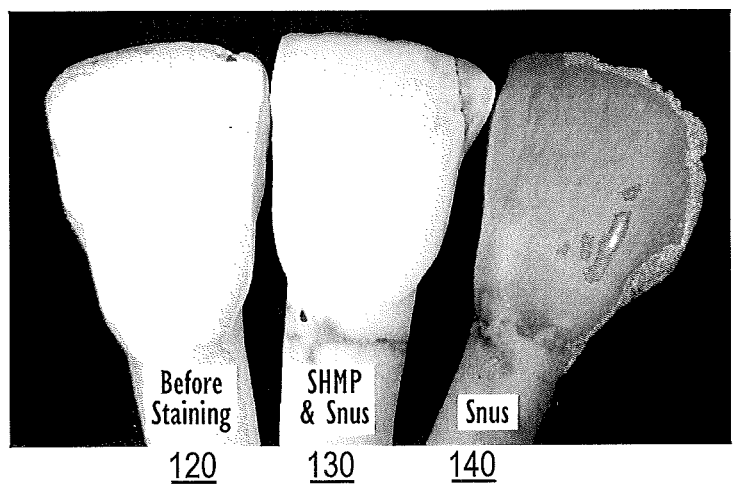
FIG. 10 is a photograph of a cow's tooth before exposure to tobacco, a cow's tooth exposed to an oral pouch product including tobacco and at least one phosphate containing stain inhibitor and a cow's tooth including tobacco and excluding a stain inhibitor.

To determine the effectiveness of the phosphate containing stain inhibitor on solid oral sensorial products including tobacco, 187.5 mL artificial saliva and 75 pouches containing 5.0 g Burley tobacco were placed in a bag in a water bath at 100° F. for 3 minutes. The artificial saliva was formed as part of a 1000 mL batch including 4.20 g sodium bicarbonate, 0.50 g sodium chloride and 0.20 g potassium carbonate. The bag was removed and rolled for about 2 minutes and then returned to the water bath for 10 minutes. This process was repeated four more times (five total). The pouches were then removed from the bag and 50 mL of the Burley tobacco extract was placed in a 250 mL crystallization beaker. Cow's teeth were then immersed in the 50 mL of extract, the beaker was covered with polypropylene wrap, and the teeth were soaked for 7 minutes at about 100° F. The teeth were removed from the beaker and rinsed with reverse osmosis water for about 5 seconds. The front enamel of each tooth was brushed with 1 g of Crest® Cavity Protection toothpaste for 30 seconds, rinsed with reverse osmosis water and covered to prevent exposure to light. This regime was repeated 4 additional times (5 total). A second extract was made using pouches including 5.0 g Burley tobacco and 50 mg sodium hexametaphosphate. A second set of cow's teeth were soaked in the Burley tobacco and sodium hexametaphosphate extract 5 times as described above. As shown FIG. 10, a cow's tooth was soaked in the Burley tobacco extract 140 is visibly darker than a cow's tooth not exposed to tobacco 120 and the cow's tooth soaked extract prepared from 50 mg of sodium hexametaphosphate and 5 g of tobacco 130.

Figure 11:
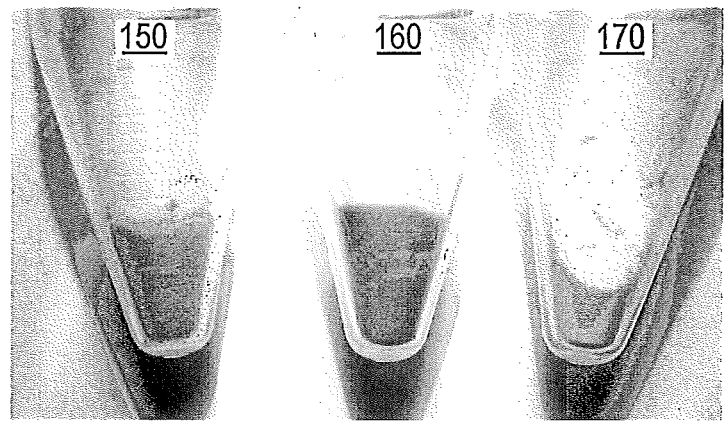
FIG. 11 is an photograph of tooth powder (hydroxyapatite) washed in dibasic sodium phosphate and soaked to Burley tobacco extract, tooth powder mixed with Burley tobacco extract and tooth powder washed in sodium hexametaphosphate and soaked in Burley tobacco extract.

As shown in FIG. 11, hydroxyapatite (HAP) powder, which is simulated tooth material, that is first washed in sodium hexametaphosphate and then soaked in Burley tobacco extract 170 is visibly whiter than HAP powder soaked in Burley tobacco extract 160 or HAP powder that is first washed in dibasic sodium phosphate and then soaked in Burley tobacco extract 150.

Figure 12:
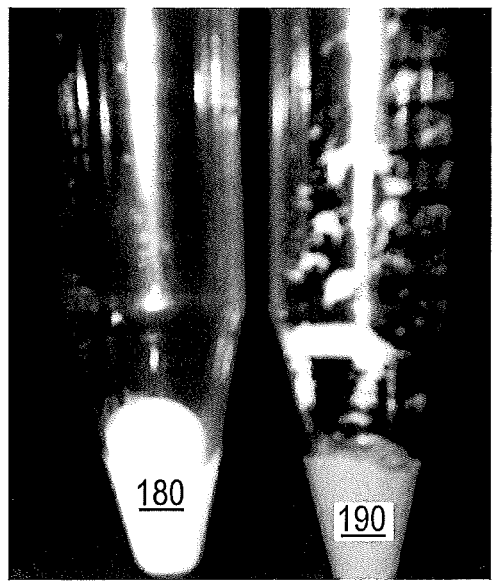
FIG. 12 is a photograph of a vial containing mixture of tea, tooth powder and sodium hexametaphosphate and a vial containing a mixture of tea and tooth powder.

To demonstrate the effect of sodium hexametaphosphate on solid oral sensorial products including tea, a first extract was formed by soaking 5.0 g of tea and 50 mg sodium hexametaphosphate in 100 mL water at room temperature for about 1 hour. A second extract was formed by soaking 5.0 g of tea in 100 mL water at room temperature for about 1 hour. Each extract was then filtered through #2 Watman filter paper. Approximately 152 mg of hydroxyapatite powder was placed in the bottom of each of two centrifuge vials. 14 mL of the first extract was placed in one vial and 14 mL of the second extract was placed in the second vial. As shown in FIG. 12, HAP powder that is soaked in the extract including tea and sodium hexametaphosphate 180 is visibly whiter than HAP powder that is soaked in the extract containing tea alone 190.

Figure 13:
FIG. 13 is a photograph of tooth powder exposed to tobacco alone and/or tobacco in combination with various amounts of sodium hexametaphosphate.

To determine the effect of various amount of sodium hexametaphosphate, 5.0 grams of Burley tobacco was soaked in 100 mL water at room temperature for 1 hour to form a first extract. A second extract was formed by soaking 5.0 grams of Burley tobacco and 25.080 g sodium hexametaphosphate in 100 mL water at room temperature for 1 hour. A third extract was formed by soaking 5.0 grams of Burley tobacco and 0.252 g sodium hexametaphosphate in 100 mL water at room temperature for 1 hour. A fourth extract was formed by soaking 5.0 grams of Burley tobacco and 0.047 g sodium hexametaphosphate in 100 mL water at room temperature for 1 hour. Each extract was then filtered through #2 Watman filter paper. Approximately 152 g of hydroxyapatite powder was placed in the bottom of each of four centrifuge vials. 14 mL of the first extract was placed in the first vial, 14 mL of the second extract was placed in the second vial, 14 mL of the third extract was placed in the third vial and 14 mL of the fourth extract was placed in the fourth vial. The powder in each vial was allowed to soak for about 1 hour with agitation and then the powder was decanted, washed in distilled water at least three times and decanted each time. As shown in FIG. 13, the powder soaked in the first extract 210 is visibly darker than the powders soaked in extracts including sodium hexametaphosphate 220, 230 and 240. Powders soaked in extracts including larger amounts of sodium hexametaphosphate are lighter in color than those soaked in extracts including smaller amounts of sodium hexametaphosphate.

In this specification, the word "about" is often used in connection with numerical values to indicate that mathematical precision of such values is not intended. Accordingly, it is intended that where "about" is used with a numerical value, a tolerance of 10% is contemplated for that numerical value. In addition, the use of geometric terms is intended to include not only the precise geometric shapes, but also similar geometric shapes that may, for example, have rounded or chamfered corners, non-linear edges, and similar departures from strict geometrical definitions.

While the foregoing describes in detail an oral tobacco pouch product with reference to a specific embodiment thereof, it will be apparent to one skilled in the art that various changes and modifications equivalents to the oral tobacco pouch product and process steps may be employed, which do not materially depart from the spirit and scope of the invention. The teachings address how certain consumers have preferences against certain tobacco flavor components (notes) and the use of at least one hydrocolloid to abate such components.

We claim:

1. A solid oral sensorial product comprising
a pouch wrapper having a coating thereon;
the coating including at least one phosphate containing stain inhibitor in an amount of about 0.001% to about 10.0% by weight based on the weight of the solid oral sensorial product;
at least one solid comprising tobacco.

2. The solid oral sensorial product of claim 1, wherein the phosphate containing stain inhibitor is selected from the group consisting of sodium hexametaphosphate, calcium hexametaphosphate, tripolyphosphate, and combinations thereof.

3. The solid oral sensorial product of claim 1, wherein the solid oral sensorial product contains about 25 mg to about 75 mg of the phosphate containing stain inhibitor.

4. The solid oral sensorial product of claim 3, wherein the solid oral sensorial product contains about 40 mg to about 60 mg of the phosphate containing stain inhibitor.

5. The solid oral sensorial product of claim 1, wherein the solid oral sensorial product weighs about 0.5 g to about 5.5 g.

6. The solid oral sensorial product of claim 1, wherein the oral pouch product comprises a filling material including at least one additional phosphate containing stain inhibitor and the at least one botanical material contained in the pouch wrapper.

7. The solid oral sensorial product of claim 1, wherein the solid oral sensorial product contains about 0.5 g to about 5.0 g of botanical material.

8. The solid oral sensorial product of claim 1, wherein the phosphate containing stain inhibitor is sodium hexametaphosphate and the botanical material is tobacco.

9. The solid oral sensorial product of claim 1, wherein the coating comprises the at least one phosphate containing stain inhibitor in an amount effective to reduce staining of teeth.

10. The solid oral sensorial product of claim 1, further comprising an acidity regulator in an amount sufficient to provide the solid oral sensorial product with a pH of about 6 to about 8.5.

11. The solid oral sensorial product of claim 1, wherein the solid oral sensorial product includes tobacco and the stain inhibitor chelates manganese and iron while maintaining the color of the tobacco.

12. The solid oral sensorial product of claim 1, comprising a tobacco filling in the pouch wrapper, wherein the tobacco filling includes at least one additional phosphate containing stain inhibitor and tobacco particles, and the tobacco filling has a moisture content of 5% to 50%.

13. The solid oral sensorial product of claim 12, further comprising a flavorant in the coating on the pouch wrapper.

* * * * *